United States Patent
Kunz et al.

(10) Patent No.: US 10,925,463 B2
(45) Date of Patent: Feb. 23, 2021

(54) NAVIGATION OF ENDOSCOPIC DEVICES BY MEANS OF EYE-TRACKER

(76) Inventors: Reiner Kunz, Kleinmachnow (DE); Michael Schmidt, Halifax (CA)

(*) Notice: Subject to any disclaimer, the term of this patent is extended or adjusted under 35 U.S.C. 154(b) by 0 days.

(21) Appl. No.: 13/203,007

(22) PCT Filed: Feb. 16, 2010

(86) PCT No.: PCT/EP2010/051945
§ 371 (c)(1),
(2), (4) Date: Nov. 7, 2011

(87) PCT Pub. No.: WO2010/097315
PCT Pub. Date: Sep. 2, 2010

(65) Prior Publication Data
US 2012/0069166 A1 Mar. 22, 2012

(30) Foreign Application Priority Data
Feb. 24, 2009 (DE) ................ 10 2009 010 263.9

(51) Int. Cl.
*A61B 1/00* (2006.01)
*G06F 3/01* (2006.01)
(Continued)

(52) U.S. Cl.
CPC .......... *A61B 1/00039* (2013.01); *G06F 3/013* (2013.01); *A61B 3/113* (2013.01); *A61B 2017/00216* (2013.01)

(58) Field of Classification Search
CPC .......... A61B 1/00; A61B 17/00; A61B 19/00; G06F 3/00
(Continued)

(56) References Cited

U.S. PATENT DOCUMENTS 5,481,622 A * 1/1996 Gerhardt et al. ............. 382/103
5,526,812 A   6/1996 Dumoulin et al.
(Continued)

FOREIGN PATENT DOCUMENTS

EP  0995142   4/2000
EP  10335369  3/2005
(Continued)

OTHER PUBLICATIONS

Ali et al., "Eye Gaze Tracking for Endoscopic Camera Positioning: An Application of a Hardware/Software Interface Developed to Automate Aesop," Studies in Health Technology and Informatics, vol. 132: Medicine Meets Virtual Reality 16, pp. 4-7, 2008.*
(Continued)

*Primary Examiner* — Daniel Chang
(74) *Attorney, Agent, or Firm* — Ladas & Parry LLP; Malcolm J. MacDonald

(57) ABSTRACT

A method for controlling image capturing and spatial control in a device monitored by imaging, in particular an endoscopic instrument, for examination and manipulation purposes, wherein the work region and the position and action of the device are monitored by means of one of the display means displaying the observed work region via optics. The device is held and moved by motor-driven equipment depending on the display, the respective position and intended action. The eye movements of the operating person or the line of sight during observation of the display is registered according to the eye-tracking method and used to control the image capturing and tracking and the display.

22 Claims, 3 Drawing Sheets

Figure 1:
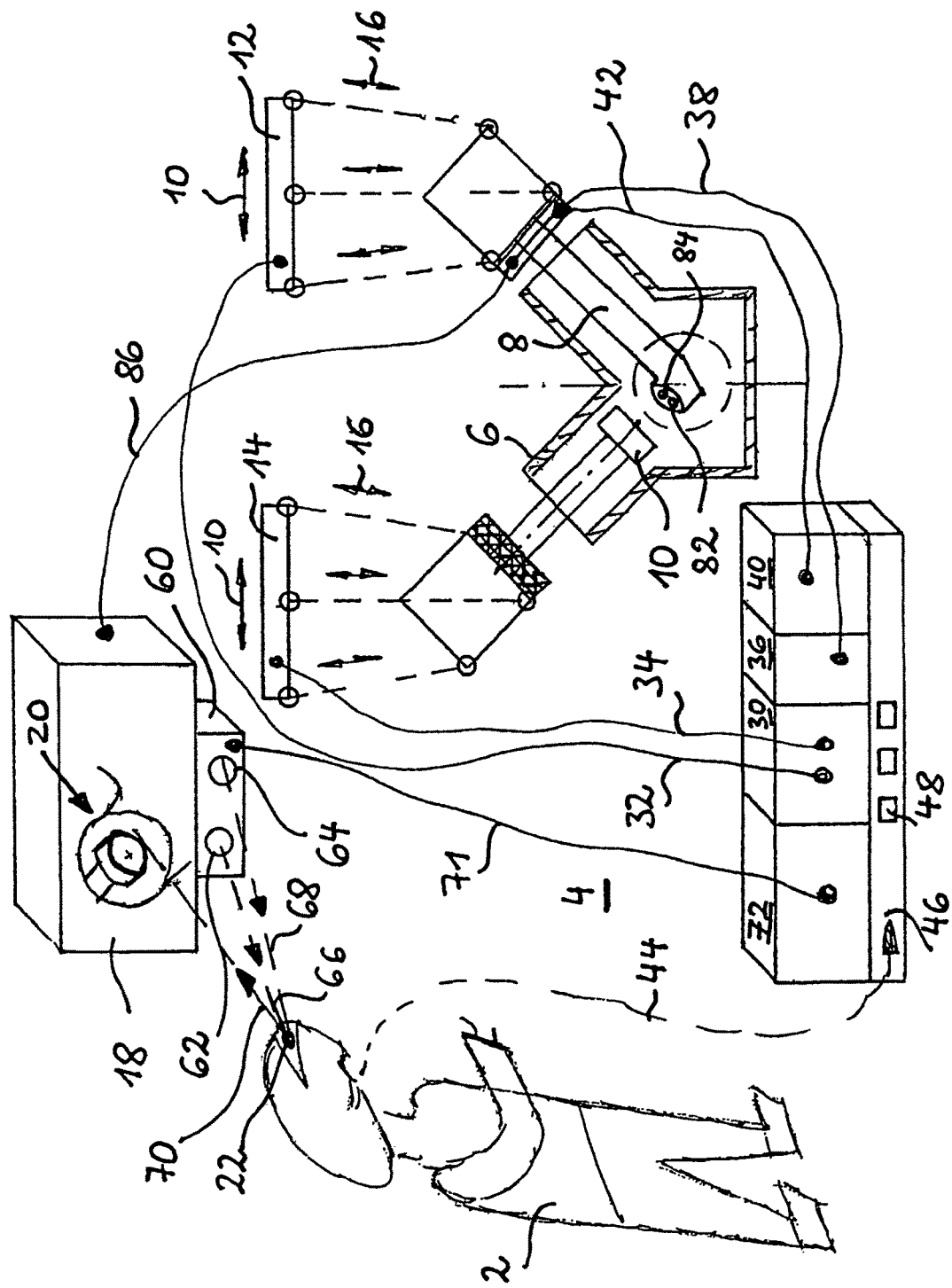

(51) Int. Cl.
*A61B 3/113* (2006.01)
*A61B 17/00* (2006.01)

(58) Field of Classification Search
USPC .......... 348/42, 45, 77, 78, 240.99; 382/103, 382/117, 128, 291; 600/101, 106, 160, 600/424, 426; 606/45, 46, 130; 359/368, 359/376, 379; 380/252; 726/17, 26
See application file for complete search history.

(56) References Cited

U.S. PATENT DOCUMENTS

| | | | | |
|---|---|---|---|---|
| 5,800,423 | A * | 9/1998 | Jensen | B25J 9/1065 606/1 |
| 5,803,082 | A * | 9/1998 | Stapleton | A61B 5/0091 600/407 |
| 5,820,545 | A | 10/1998 | Arbter et al. | |
| 5,836,869 | A * | 11/1998 | Kudo | A61B 1/00039 600/173 |
| 5,867,308 | A * | 2/1999 | Pensel et al. | 359/368 |
| 5,876,325 | A * | 3/1999 | Mizuno | A61B 34/37 600/102 |
| 5,912,721 | A * | 6/1999 | Yamaguchi | G06K 9/0061 351/209 |
| 6,043,890 | A * | 3/2000 | Spink et al. | 356/614 |
| 6,154,315 | A | 11/2000 | Street | |
| 6,243,076 | B1 | 6/2001 | Hatfield | |
| 6,406,472 | B1 | 6/2002 | Jensen | |
| 6,456,262 | B1 * | 9/2002 | Bell | A61B 3/113 345/472 |
| 6,463,361 | B1 * | 10/2002 | Wang | G16H 40/63 700/258 |
| 6,578,962 | B1 * | 6/2003 | Amir | A61B 3/113 345/157 |
| 6,847,336 | B1 * | 1/2005 | Lemelson et al. | 345/8 |
| 7,561,143 | B1 * | 7/2009 | Milekic | G06F 3/013 345/156 |
| 7,641,609 | B2 * | 1/2010 | Ohnishi et al. | 600/117 |
| 8,238,513 | B2 * | 8/2012 | Ma | 378/6 |
| 2002/0156345 | A1 | 10/2002 | Eppler et al. | |
| 2005/0199783 | A1 | 9/2005 | Wenstrand et al. | |
| 2005/0228256 | A1 * | 10/2005 | Labadie | A61B 90/10 600/407 |
| 2006/0100642 | A1 * | 5/2006 | Yang et al. | 606/130 |
| 2007/0182929 | A1 * | 8/2007 | Feher | A61B 3/113 351/243 |
| 2007/0265495 | A1 * | 11/2007 | Vayser | A61B 1/045 600/109 |
| 2008/0144773 | A1 * | 6/2008 | Bar-Zohar | A61B 6/5247 378/98.12 |
| 2008/0247616 | A1 | 10/2008 | Pescatore et al. | |
| 2008/0297590 | A1 * | 12/2008 | Barber | H04N 13/383 348/47 |
| 2009/0141895 | A1 * | 6/2009 | Anderson et al. | 380/252 |
| 2009/0202114 | A1 * | 8/2009 | Morin | A63F 13/213 382/118 |
| 2009/0245600 | A1 * | 10/2009 | Hoffman | A61B 1/00039 382/128 |
| 2009/0248036 | A1 * | 10/2009 | Hoffman | A61B 1/045 606/130 |
| 2011/0202842 | A1 * | 8/2011 | Weatherly | G06F 8/38 715/716 |
| 2011/0270123 | A1 * | 11/2011 | Reiner | A61B 3/113 600/558 |

FOREIGN PATENT DOCUMENTS

| | | |
|---|---|---|
| JP | 05-211988 | 8/1993 |
| JP | 07-328016 | 12/1995 |
| JP | 10-290392 | 10/1998 |
| WO | 2007050029 | 5/2007 |
| WO | 2008066460 | 6/2008 |

OTHER PUBLICATIONS

Noonan et al "Gaze Contingent Articulated Robot Control for Robot Assisted Minimally Invasive Surgery", 2008, IEEE/RSJ International Conference . . . , pp. 1186-1191, Sep. 22, 2008.

Kim et al "Smart Colonoscope System", 2002 IEEE/RSJ International Conference . . . , pp. 1367-1372, Sep. 20, 2002.

* cited by examiner

NAVIGATION OF ENDOSCOPIC DEVICES BY MEANS OF EYE-TRACKER

This application is a 371 of PCT/EP2010/051945 filed on Feb. 16, 2010, which is incorporated herein by reference.

The invention relates to the control of image acquisition and the control and navigation of devices for implementing observations and interventions in cavities, channels and passages within a body or object. The invention relates in particular to a method for image acquisition in the case of an endoscopic device monitored by means of image transmission, or of an instrument comprising an endoscopic device for examination and manipulation purposes, wherein the working region of the endoscopic device or instrument is observed via optics and is displayed by a display means and the position and action of the endoscopic device are monitored via the display means, wherein the endoscopic device is held and moved by a motor-driven device depending upon the image representation on the display means, the respective position and intended action.

In the case of such a method described in DE 195 29 950 C1 a stereo laparascope for minimally invasive surgery is moved by means of a robot. The robot drive is controlled via surgical instruments located in the surgical area, observed on a monitor and marked in colour for their position to be determined. The surgical instruments are always displayed in the central area of the observing monitor. This mode of representation is based on the assumption that the tip of the monitor-observed surgical instruments marked in colour also corresponds to the central area of the desired image representation. The section of the image representation is thus defined via the centred representation of a colour marking by means of bi-ocular optics.

There is known from DE 10 2004 063 566 A1 a control system having an image generator and eye detection processing by means of which an apparatus, e.g., a light source, can be switched on, off or over. The control system can also be used for example to switch the polarisation of a window.

DE 197 31 301 A1 describes a microscope controller for use in eye operations, wherein a viewing direction analysis of the microscope user is used for controlling devices. In an eyepiece tube, viewing position data of the viewer are obtained in an intermediate image plane on a working field and are calibrated in a processor, wherein the microscope magnification and the size of the working field are converted. The resulting data are transmitted to a control unit.

DE 199 83 513 B4 relates to a method for selecting a moving graphical object represented on a screen of a computer, wherein the eye movements of the user are monitored and are compared with the object movement. The computer determines the function which the user wishes to perform and then performs it. This can be screen-controlled computing applications or applications for disabled people in order to provide them with access to computer resources with minimal or no use of hands. Further applications include the control and operation of air and ground vehicles, e.g., of visual displays in aeroplanes, furthermore in monitoring centres and also in simulators and entertainment systems.

WO 2008/066460 A1 discloses a controller having an image capture device and a processing unit connected thereto. This supplies an eye position signal for controlling a light source. WO 2007/050029 A2 by the same Applicant relates to interaction, controlled by eye-tracking, with a computer, wherein commands are input via a graphical data manipulation field on the computer monitor by means of eye-tracking and are further processed in the computer. In this manner a cursor can be moved or data inputs can be implemented, e.g., text can be written or processed.

Figure 2:
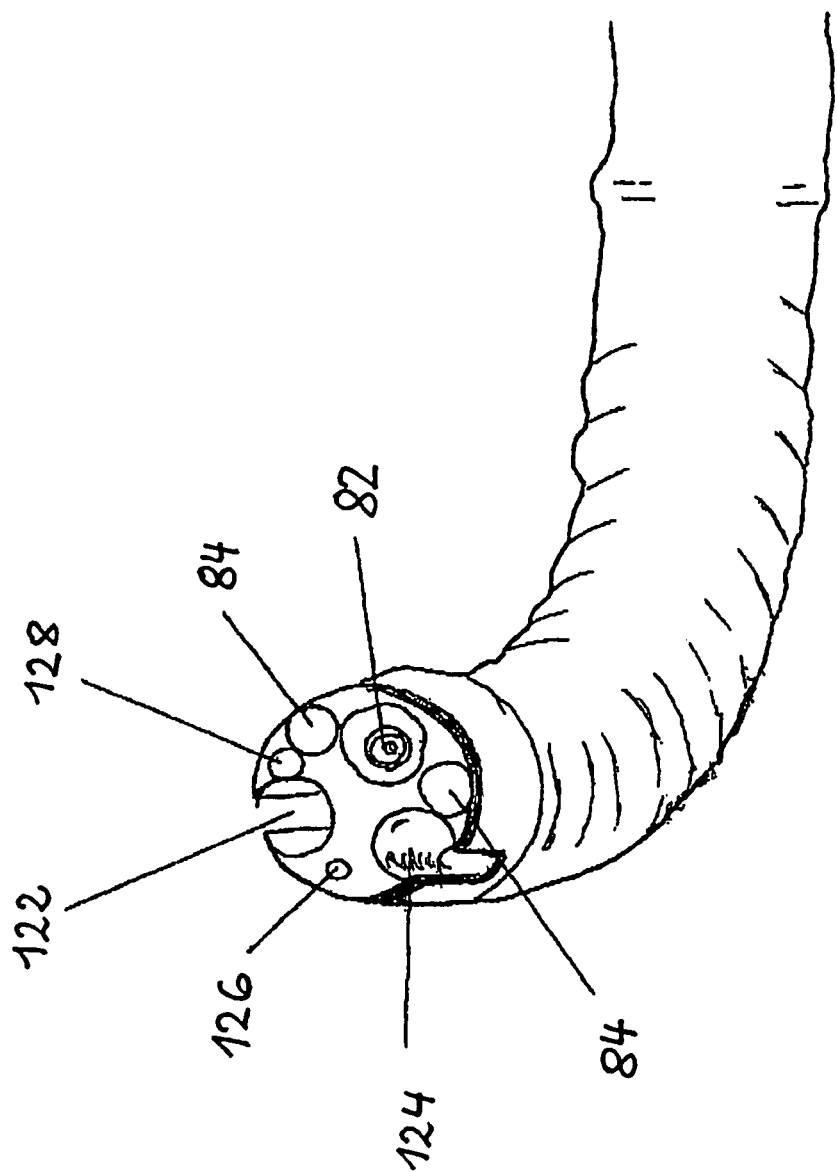

In the field of medicine and technology, typical applications include those in which objects are reflected by means of flexible and rigid endoscopes. In addition to direct sight, continuing examination or manipulation of the region to be examined occurs via inner working channels or additional, inserted working actuators independent of the endoscope. Flexible endoscopes directed by Bowden cables are used and provide an image of the working region or object to be examined. FIG. 2 shows by way of example the distal end of a video endoscope 120 with bendable working channels 122, 124, video optics and objective 82, light conductors 84 for illumination, nozzles 126, 128 for insufflation and flushing or cleaning of the objective.

There are known in the technical field non-destructive inspection and measurement (non-destructive testing) by means of rigid and flexible endoscopes as well as by additionally introduced probes of the most varied test procedures from motor and turbine technology, air and space travel, quality control, the building trade and construction.

When working with an endoscope, an object is generally observed via an image converter chain having a visual display. The viewer can then observe the object to be examined in a spatially remote manner via an image converter using data transfer.

By way of example, this is described in medicine for minimally invasive surgery: the user, i.e., the person operating the endoscope, observes the image which is obtained by the image-acquiring endoscope and is reproduced on a monitor, wherein the endoscope is stabilised and guided either by the user himself or by a camera assistant, a holding system or an operations robot or the like. The monitor can be positioned in proximity to the area of examination or can be placed remote from the action using data transfer. People assisting the user support him, in that they assume partial or additional functions in endoscope guidance or in implementing additional manipulations in order to be able to perform complex work and tasks. This is frequently effected in a purely manual manner, e.g., by an assistant. The assistants perform their tasks upon being requested or independently. Fatigue, concentration or communication problems can considerably impair the interaction of the users which results in corresponding disruption of the course of action.

There are various systems which allow the endoscope or the additional instruments or operating tools to be adjusted, moved, positioned and kept in the desired end position. These are either directly manually moved or are motor-driven, controlled via input commands. For the purpose of inputting commands, there are known e.g., keypads, a joystick, operating pad or even voice control.

The object of the invention is to use the image representation, which is required for spatial navigation and for representing an examination and manipulation region, preferably also to guide—in a wholly or partly automated manner—some of the instruments, i.e., to guide the representation of the examination space or to move instruments or objects, to bring them into position and keep them there.

This object is achieved by the invention in the case of a method having the features of claim 1 and an apparatus having the features of claim 18. Advantageous developments of the method in accordance with the invention and apparatus are the subject matter of the subordinate Claims.

The invention thus relates to a method for the spatial control and navigation of a device for implementing observations and interventions in cavities, channels and passages within a body or item, in particular an endoscopic device or an instrument comprising an endoscopic device. The device is provided with imaging means or its position can be detected using imaging means. A display means is provided. The device is moved depending upon the representation of observation images on the display means, the respective position and intended action. The eye movements of the operating person when observing the image representation on the display means are detected in accordance with the eye-tracking method and are used to control the device and its function.

The method in accordance with the invention is thus used to control the image guidance and an instrument, in particular an endoscopic instrument, by the user himself. This means that the user observes, by means of an image converter chain, the representation and working region or an object which are represented on a display of an image which has been produced in particular endoscopically. When observing this image, the eye movements of the user are tracked in an automated manner by means of eye-tracking and the user can direct the image representation and device navigation to the targets of interest to him by means of eye-tracking control. A monitor or even a projection device can be provided as the display means. Optionally, a 3D representation can also be selected.

The imaging means are different depending upon the respective field of application. They can be based on X-rays, particle rays, radiography, computer tomography, magnetic resonance processes, ultrasound processes, visible light and infrared rays and also further imaging methods. Devices operating in an endoscopic manner and with optical means are widely used. However, the invention is not limited to such devices and applications, in particular the use of endoscopes and endoscopic devices, but also relates, as stated, to instruments equipped with such devices. Other display devices and instruments can also be used instead of endoscopic devices, wherein ultimately the imaging means are selected depending upon the usage application and location. For example, in the case of a cardiac valve replacement, the intervention (introduction and anchoring of the cardiac valve) can be performed in a minimally invasive manner, radiologically using X-ray image converter control. In other cases, the use of ultrasound probes as a display device can be preferred. The devices and instruments are controlled by means of eye-tracking.

In a preferred embodiment variant of the method in accordance with the invention, a camera is expediently used for the image acquisition and is moved via eye-tracking and/or its adjustments are controlled via eye-tracking. In the case of a flexible video endoscope, the camera objective is located in the flexible endoscope tip. However, the image acquisition can also be effected via a light conductor and a camera, CCD chip etc. disposed downstream thereof. They are also to be encompassed by the term "camera". Along with the camera or optics guidance, the endoscopic instrument or the tip thereof is simultaneously guided in a manner controlled by eye movement, i.e., it is moved forwards, moved backwards and optionally also pivoted to the side. In an advantageous manner, the image acquisition is centred on the eye movement, i.e., the main viewing axis is directed towards the working region or the object of interest and this is shown in the centre of the reproduced image. The endoscope having the imaging video camera is guided correspondingly to the eye movements of the user until the targeted object is in the centre of the acquired and reproduced image and the eyes of the user directed towards the object of interest or the viewing axis are directed to the centre of the monitor image.

In this manner it is possible to use the eye-tracking technology to guide endoscopes or other devices inserted into cavities, channels and the like as well as additional instruments with direct control of the fixing of the view of a user to a "region of interest" in the generated image without a time delay and communication problems.

The observer can be located spatially remote from the observed object using the method in accordance with the invention. Using endoscopy or as stated with instruments equipped accordingly it is possible to observe cavities, channel, surfaces, etc. optionally from afar or to perform interventions therein or thereon. The invention allows additional instruments to be controlled in complex interventions. Actions can be performed on the observed objects or materials and items can be introduced or local things can be manipulated or changed. These include inter alia catheters, stents, measuring probes, in particular also tubes and other flexible lines such as e.g., breathing tubes, valve systems, clip fasteners and other examination and treatment materials. By using eye-tracking and the imaging means for control and navigation in accordance with the invention, the operation of the device or object introduced into the cavity or e.g., channel can be simplified or it is possible for an external specialist who is at a different location to become involved in the process.

It can be expedient to reproduce the object image in a defined area of the display means which is not central but rather lies eccentrically in the illustrated observation image so that in this case the image acquisition centre and the viewing axis diverge. The object is then detected eccentrically in the image acquisition and is correspondingly reproduced eccentrically on the display means. In this manner, applicators (operating instruments) etc. located in the image acquisition area can be captured, reproduced in the centre of the display, i.e., on the image illustrated on the display means, and the applicators can be hereby observed and/or handled effectively. Thus, when using the method in accordance with the invention, in a preferred manner not only the camera is controlled but also one or more applicators of the e.g., endoscopic device can be held and guided in a manner controlled by means of the eye movements. For this purpose, provision is made that the eye-tracking control is switched form controlling the image (image acquisition and guiding) to any other auxiliary means, e.g., for instrument guidance, for actuating the e.g., endoscopic instrument, on an applicator (e.g., alligator forceps), wherein the other device or instrument is then guided and actuated in a manner controlled by the eye-tracking. In other words, in this case firstly the endoscope itself is positioned and then fixed in a manner controlled by eye-tracking. The control is switched to the operating instrument and this is subsequently positioned by eye-tracking and the relevant instrument is actuated.

A switch is made for example when the intended position of the endoscopic instrument has been reached, i.e., when the object of interest is reproduced as required on the display means. Then, the position of the endoscopic instrument and the display of the relevant working region are frozen. The eye-tracking can then be used to control an instrument located in the image area. This is e.g., expedient in colonoscopy in which the base of a detected polyp is eccentrically illustrated whilst the intestinal lumen remains aligned in the centre of the monitor. A switch can then be made to operation of an additional instrument and this can be operated via eye-tracking. Thus during colonoscopy, a detected polyp can be removed at this point in that either the tip of the endoscope is also moved to the intestinal wall or the relevant operating channel is bent and the endoscope loop is put over the polyp via eye-tracking.

After switching the eye-tracking function from one device to the next and also after freezing a position reached, the instrument no longer guided/controlled by eye-tracking is fixed in position as if it were securely held by an assistant. Communication problems are obviated, the user thus has the ability to control the endoscope/image guidance as well as individual actuators independently. As soon as the image area needs to be changed, the eye-tracking system is then to be re-activated for image representation and the camera or observation optics are to be moved as explained above. Since for each frozen position, during this state, the eye-tracking system is not used, there is the option to alternatively control different instruments successively using the system.

In the case of the eye-tracking system used for implementing the method in accordance with the invention, the camera required for detecting eye movements or the viewing axis of the eyes can be placed e.g., on a headset, on the monitor or at a location suitable for detecting the eye movements.

In the case of one method variant, a guide marking is projected from the image-acquiring endoscope or other display device, which marking marks the centre of the image acquisition optics and thus the acquired image. The eye-tracking focuses on this one guide marking which is normally displayed in the centre of the image representation on the display means. A light spot or light beam e.g., from a laser pointer, located in the focusing axis of the video objective can be used as the guide marking. The laser beam can also simultaneously be used to measure the distance—for example by means of an optical distance measuring system—between the optics system and the observed object/instrument or the viewed area and thus for the three-dimensional navigation. The marking and thus the camera or image area can be displaced by eye-tracking.

In the case of a preferred method variant, the eye-tracking control signal is processed with adjustable inertia. This allows the control signal to compensate for effects having a negative influence such as eye flickering (nystagmus).

Provision is preferably made for the auto-focusing device, the magnification adjustment and/or the distance measurement from the tip of the device to the observed object to be selected and/or engaged by means of eye-tracking.

The command inputs for a device, instrument or additional instrument to be controlled by eye-tracking, in particular the selection of an instrument, the switching to the instrument or switching the instrument setting, can be implemented by voice-control or even by operating means, in particular a joystick, keypads, operating pad.

By way of example, in the case of endoscopic examinations and manipulations which are effected in a guided manner by an operating person (user) via the screen, the following options are produced by eye-tracking:

1. The image-acquiring optics system can be positioned via corresponding holding and guiding units in a manner controlled by eye-tracking. Via additional functions, it can be defined that the view detection of the user advances the viewing point/"region of interest" into the centre of the image area and this is thus positioned in the centre of the monitor. Alternatively, the location of interest can lie outside the image centre, i.e., it remains eccentric in the generated image. The eccentric image detection is provided when an operating means located in the image area is to be controlled by the user via eye-tracking. The control and positioning of the operating means in relation to the object which is eccentric in the image can be facilitated in this manner.

2. By switching the control from the image guidance to an instrument or another, second (or third) instrument, the endoscope or respective first instrument is fixed in position. The selected instrument can be any auxiliary means which is located in the image area of the endoscope and has to be positioned/manipulated. This can also refer to additional examination instruments or even materials or items which are visualised via endoscopes and are introduced temporarily or permanently into (body) cavities, vessels or hollow organs in a manner controlled by the user using eye-tracking, or in the field of technical endoscopy it can correspond to examination and manipulation techniques in terms of non-destructive testing.

The user can himself directly control operations by eye-tracking, which operations were previously effected by assistants. Possible communication problems in teamwork can be obviated and no, or few, assistants are required.

Figure 3:
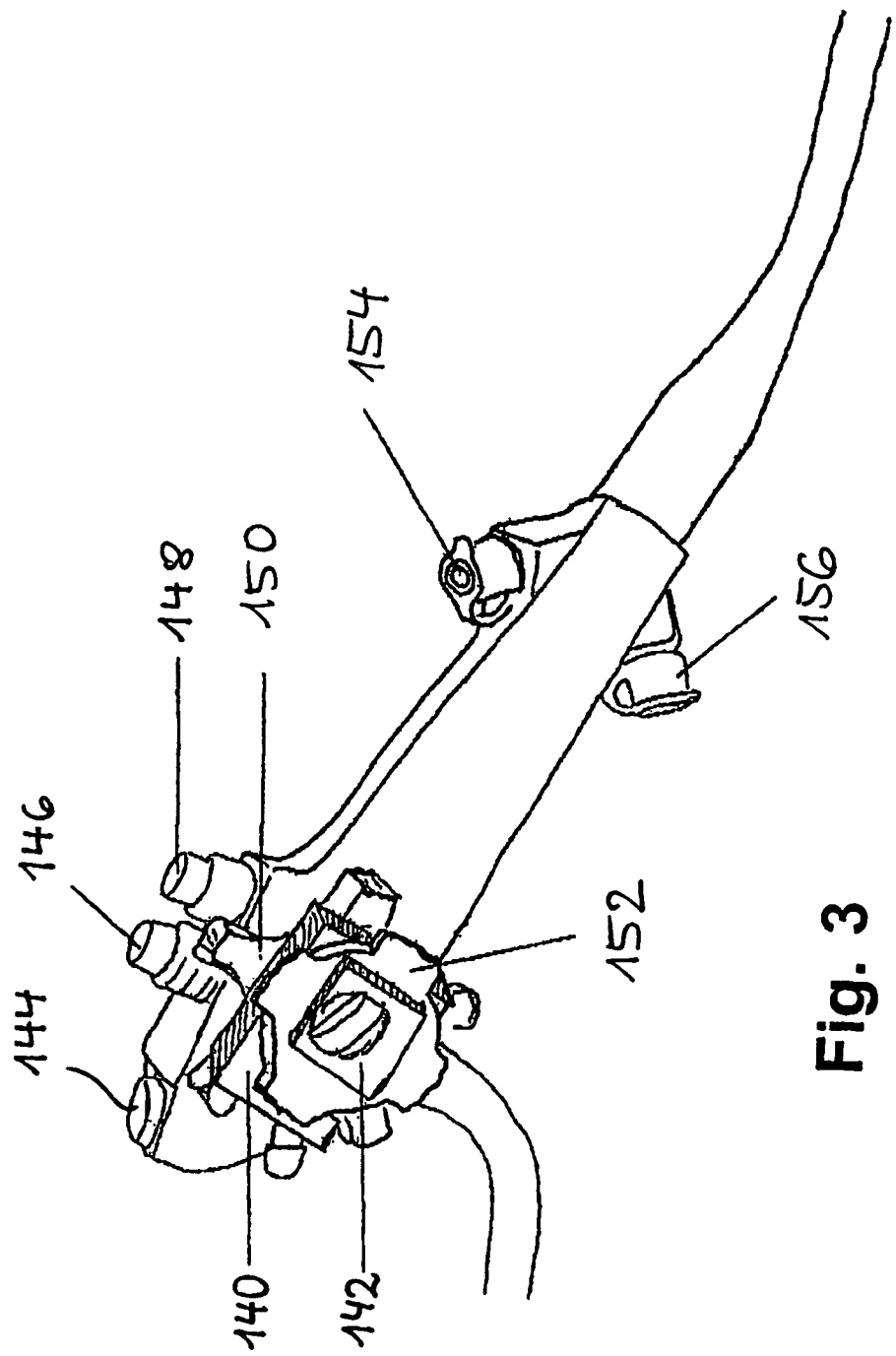

The invention will be described hereinafter with the aid of an exemplified embodiment and the drawings. This depiction is used merely for illustrative purposes and is not intended to limit the invention to the specifically provided feature combinations. In the drawings:

FIG. 1 shows a schematic view of a structure for endoscopic testing and manipulation using the method in accordance with the invention, FIG. 2 shows a schematic partial illustration of the distal end of a flexible endoscope, and FIG. 3 shows a schematic illustration of the control body of the flexible endoscope.

An exemplified embodiment of the invention will be explained hereinafter with the aid of FIG. 1 which shows an endoscope operating environment. A user 2 stands in an examination room 4 in which a object 6 to be examined is located. An endoscope 8 fitted with different devices and an operating instrument 10 illustrated close to the item under examination are located in the operating position in an operating area and are attached to a holding and positioning device 12, 14 which can be moved in the direction of arrows 16.

The endoscope 8 designed as a video endoscope is described in more detail hereinafter with the aid of FIGS. 2 and 3. The tip of the endoscope 8 shows two channels 82, 84. The channel 82 contains a video cable, not illustrated, and an objective having an auto-focusing function for image acquisition. Located in the channel 84 are fibre optics for the illumination of the working or operating area 20 and also marking devices. An e.g., projected guide marking, not illustrated, is located on the item (object) under examination. The endoscope 8 further includes two working channels 122, 124 and a jet nozzle 126.

Located on the control body, illustrated in FIG. 3, of the flexible endoscope are the actuating members or connections for operation and control thereof. The eye-tracking drive 140, 142 is disposed on the manipulation end of the control body and contains a right/left and up/down unit. A push button 144 is provided for switching between manual control and eye-tracking control. Function buttons 146, 148 are provided for suction or flushing/insufflation. Levers 150, 152 can be used for the manual up/down and right/left control. Connections to working channels are designated by the numerals 154 and 156.

The holding and positioning device 12, 14 or its drive is connected to a controller 30 via control lines 32, 34 for guiding and positioning the endoscope 8 and actuating it.

The endoscope 8 is connected to control electronics 36 via a control line 38. A cold light source 40 is connected to the endoscope 8 or its illumination channel 84 via light conductors 42.

The user 2 looks at a monitor 18 which in the illustrated exemplified embodiment is suspended above the operating table as a display means. This monitor shows a video image of the operating area 20 which is supplied from the endoscope 8 via an image converter chain 86. An audio input 46 and an input field 48 are provided on the central control unit for possible voice input (arrow 44) and manual input, which central control unit also contains further control units 30, 36, 40, 72. However, the movements of the endoscope 8 are not generally controlled and implemented manually but by means of eye-tracking. For this purpose, located beneath the monitor 18 is an eye-tracking observation unit 60 having an infrared light source 62 and a video camera 64 which point towards the eyes 22 of the user 2 (arrows 66, 68) as part of a commercially available eye-tracking system. The user 2 observes the illustrated area 20 on the monitor 18 (arrow 70) and the video camera 64 observes the eye movements, wherein evaluation takes place in a computer of the eye-tracking controller 72 connected via a control line 71, the output control signals of the eye-tracking controller being sent to the controller 30 of the holding and positioning device 12, 14.

This structure allows the user 2 to operate, at least in the case of relatively simple manipulations, without assistants. For complex interventions in which e.g., image-acquiring endoscopes having multiple working channels are used, it is thus no longer necessary to use 3 to 4 assistants for operating the different instruments whose actions have to be precisely adapted to each other and to the user. Rather, the user for example can move the endoscope tip (of a flexible endoscope) via two control wheels when the target object is reached and can adjust the image whereas assistants push, pull, open and close etc. examination instruments, biopsy forceps, pincers etc. via working channels with the corresponding co-ordination problems of several people working on the same object.

The different operative working steps of the user can be performed by him successively using the eye-tracking controller whilst the positions of the instruments and views which are not yet required are frozen. For example, in the case of polyp removal in the large intestine, the main image is frozen and the eye-tracking is controlled with the eyes for another function such as pushing or moving the removal loop around the polyp stem.

The invention claimed is:

1. A method for the spatial control and navigation of an endoscopic device, the method comprising:
   providing the endoscopic device with an imaging means, or detecting a position of the endoscopic device using an imaging means,
   providing a monitor,
   moving the endoscopic device, depending upon at least one of a representation of observation images on the monitor, a position of the endoscopic device, and an intended action,
   detecting eye movements of an operating person when observing the representation of observation images on the monitor in accordance with an eye-tracking method, and using the detected eye movements to move the endoscopic device spatially, and
   using eye-tracking to select or engage, or to both select and engage, at least one of an autofocusing device, a magnification adjustment, and a distance measurement from a tip of the endoscopic device to an observed object;
   wherein the eye-tracking controls the endoscopic device;
   wherein the eye-tracking controls a switching from the endoscopic device to an instrument, and a guiding and actuation of the instrument; and
   wherein the endoscopic device is frozen in position when the control of the endoscopic device by eye-tracking is switched to the control of the instrument by eye-tracking; and/or wherein the instrument is frozen in position when the control of the instrument by eye-tracking is switched to the control of the endoscopic device by eye-tracking.

2. The method according to claim 1, wherein the image acquisition is centered by the eye movement.

3. The method according to claim 1, wherein the image acquisition of a working area and the associated image representation are captured and maintained on the monitor, and one or more details in the working area are selectively viewed using the eye-tracking, wherein the respective image representation of a viewed section illustrated eccentrically on the monitor is centered by the eye-tracking.

4. The method according to claim 3, wherein the tip of the endoscopic device, or a working channel of the endoscopic device, is guided to the viewed section of the working area.

5. The method according to claim 1, wherein the imaging means operates using X-rays, radiography, computer tomography, magnetic resonance processes, ultrasound processes, visible light, or infrared rays.

6. The method according to claim 1, wherein a camera is used for the image acquisition, and the camera is moved via at least one of eye-tracking and adjustments controlled via eye-tracking.

7. The method according to claim 1, wherein a guide marking is projected from the endoscopic device, and wherein the guide marking marks a center of the image acquisition.

8. The method according to claim 7, wherein a light spot or light beam is used as the guide marking and the light beam is used to measure the distance between the optics and object area.

9. The method according to claim 8, wherein the measured distance is used as a control variable for navigation of the endoscopic device.

10. The method according to claim 1, wherein the eye-tracking control signal is processed with adjustable inertia to the eye movement of the operating person.

11. The method according to claim 1, wherein the eye-tracking controller is switched from image acquisition and guidance to at least one of actuation or guidance of the endoscopic device and the actuation of endoscopic applicators, additional instruments, or an auxiliary means.

12. The method according to claim 1, wherein a drive of the endoscopic device is controlled by eye-tracking and the endoscopic device is actuated by eye-tracking.

13. The method according to claim 1, wherein one or more applicators of the endoscopic device or an auxiliary means are guided or actuated, or both, in a manner controlled by eye-tracking.

14. The method according to claim 1, wherein at least one of the introduction of materials, items in the working or examination space, and the removal of object material and samples from the working or examination space, is controlled by means of eye-tracking.

15. The method according to claim 1, wherein the input of commands for the endoscopic device, comprising at least one of a selection of the endoscopic device, a switching to the endoscopic device, and a switching of a setting of the endoscopic device is implemented by eye-tracking.

16. A device for image representation and for spatial control and navigation of an endoscopic device, the device comprising:
- an endoscopic device having an imaging means observing a working area of the endoscopic device;
- a monitor which displays the working area of the endoscopic device and its position and action in the working area;
- a drive device which can be motor-driven and holds and moves the endoscopic device spatially, depending upon the monitor, the respective position and intended action by an operating person,
- a detection device for detecting the eye movements of the operating person when observing the working area on the monitor in accordance with an eye-tracking method,
- wherein the detection device outputs an output signal for controlling the image acquisition, for controlling the image guidance, and the reproduction on the monitor,
- wherein, by means of an eye-tracking signal output by the detection device, at least one of a selection and engagement of the auto-focusing device, a magnification adjustment, and a distance measurement from the endoscope tip to the observed object is performed; and
- wherein, by means of an eye-tracking signal output by the detection device, a control of an endoscopic device is provided;
- wherein the eye-tracking controls a switching from the endoscopic device to an instrument, and a guiding and actuation of the instrument; and
- wherein the endoscopic device is frozen in position when the control of the endoscopic device by eye-tracking is switched to the control of the instrument by eye-tracking;
- and/or wherein the instrument is frozen in position when the control of the instrument by eye-tracking is switched to the control of the endoscopic device by eye-tracking.

17. The device according to claim 16, wherein the imaging means operates using X-rays, radiography, computer tomography, magnetic resonance processes, ultrasound processes, visible light, or infrared rays.

18. The device according to claim 17, wherein the imaging means includes optics which observe the working area of the device and have a light source, wherein the imaging focuses automatically.

19. The device according to claim 16, wherein an operating area can be overlaid on the monitor and can be selected and engaged via the control functions.

20. The device according to claim 16, wherein a navigation controller is provided for at least one of the devices for image representation and additional instruments.

21. The device according to claim 16, wherein the spatial movement of the endoscopic device is three-dimensional movement.

22. The method according to claim 1, wherein the endoscopic device is moved three-dimensionally.

* * * * *